United States Patent [19]

Scott

[11] Patent Number: 4,702,238

[45] Date of Patent: Oct. 27, 1987

[54] EARPLUG

[76] Inventor: Robert T. Scott, 416 Lighthouse Ave., Santa Cruz, Calif. 95060

[21] Appl. No.: 847,676

[22] Filed: Apr. 3, 1986

[51] Int. Cl.$^4$ ............................................. A61F 11/00
[52] U.S. Cl. .................................................... 128/151
[58] Field of Search .................... 128/151, 152; 2/423; D24/67; 181/129, 130, 133, 132, 135

[56] References Cited

U.S. PATENT DOCUMENTS

| | | | |
|---|---|---|---|
| 904,715 | 11/1908 | McWilliams | 128/151 |
| 1,016,877 | 2/1912 | Elliott | 128/152 |
| 1,335,276 | 10/1920 | Schultz | 128/152 |
| 2,881,759 | 4/1959 | Hocks et al. | 128/152 |
| 3,415,246 | 12/1968 | Hill | 181/130 X |
| 3,833,701 | 9/1974 | Johnson et al. | 128/152 X |
| 4,160,449 | 7/1979 | Wade | 128/152 |
| 4,537,187 | 8/1985 | Scott | 128/151 |
| 4,582,053 | 4/1986 | Wilson | 128/152 |

*Primary Examiner*—Robert A. Hafer
*Assistant Examiner*—Kathleen J. D'Arrigo

[57] ABSTRACT

An earplug for attenuating sound and providing a watertight seal at the auricle is provided which is made of solid, closed cell, slow recovery foam having an external flange adapted to extend beyond the auricle, the surface of the plug being convex to reflect away sound, and having an inwardly extending conical portion fitting into the auricle or cavum concha and the outer portion of the auditory canal sealing off the meatus of the external ear canal without substantially penetrating the external ear canal. The closed cell foam provides a multitude of convex and concave surfaces which dramatically reflect, dissipate and attenuate sound waves.

3 Claims, 5 Drawing Figures

EARPLUG

CROSS-REFERENCE TO RELATED APPLICATION

This application is an improvement of application Ser. No. 539,483, now U.S. Pat. No. 4,537,187 dated Aug. 27, 1985.

SUMMARY OF THE INVENTION

The present invention relates to an improved form of earplug. The earplug of the present invention is an improvement upon U.S. Pat. No. 4,537,187 in which a solid piece of slow recovery, closed cell foam is utilized to dissipate and attenuate the energy of sound waves.

The present invention is primarily adapted for use in sound attenuation to protect the inner ear cochlea from excessive noise in industry including exposure to jet engine noise and gun fire.

The present invention also provides a watertight seal and therefore may be used by swimmers, surfers and the like to keep water out of the ear canal. It may also be used by children with ventilation tubes to keep water out of the ear canal and middle ear.

The outer surface of the present earplug is convex to reflect sound waves away and to provide more bulk for the internal closed cells to dissipate sound energy.

A further feature of the invention is the use of reaction injection molding which produces a skin covering the entire plug rendering it nearly impervious to dirt and water. This smooth surface lends itself to washing with soap and water and cleansing with alcohol.

Various other objects and features of the invention will be brought out in the balance of the application.

DESCRIPTION OF THE PREFERRED EMBODIMENT

Figure 1:
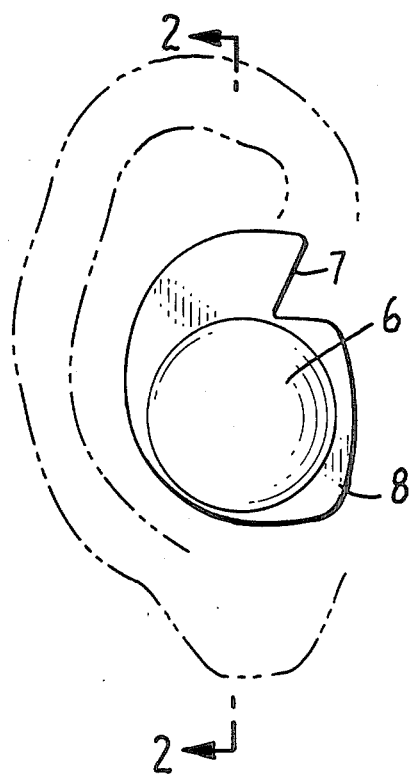
FIG. 1 is an elevational view from the outside of the user's ear showing the plug embodying the present invention.

In the drawings forming a part of this application, the plug of the present invention is shown in solid lines while the ear of the user is shown in phantom. The plug of the present invention has an external flange 5 extending beyond the auricle or cavum concha 11, the outer surface 6 of said plug being convex in order to reflect away sound and to provide increased bulk which in turn provides more internal closed cells for dissipating sound energy. A conical portion 9 is adapted to fit against and seal the auricle or cavum concha 11. At the inner end of the plug is a flat portion 13 with a rectangular surface which fits into the auditory canal 17 without substantially penetrating the external ear canal. A small external double flange 15 forming a rectangular knob is provided at the inner end of the plug which helps seal off the meatus of the external ear canal. The preferred form uses a double flange as shown, although a single flange could also be used. Flange 5 has a side 7 adapted to fit against the crus helix, and anti-helix and a side 8 adapted to fit against the tragus.

By not substantially penetrating the exterior canal, the present invention avoids impaction of the ear wax into the depths of the external ear canal.

An airtight and watertight seal is formed by conical portion 9 bearing against the auricle or cavum concha 11.

Figure 2:
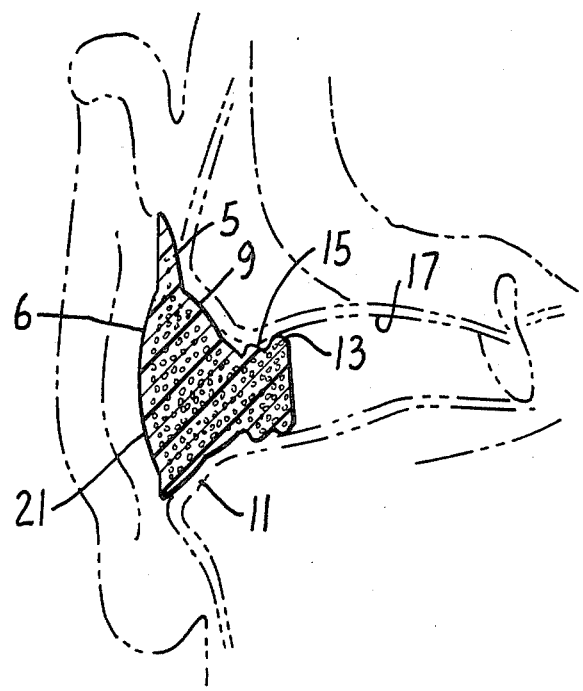
FIG. 2 is a section on the line 2—2 of FIG. 1.
Figure 3:
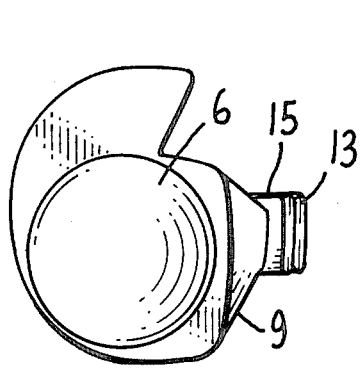
FIG. 3 is a front perspective view of the plug.
Figure 4:
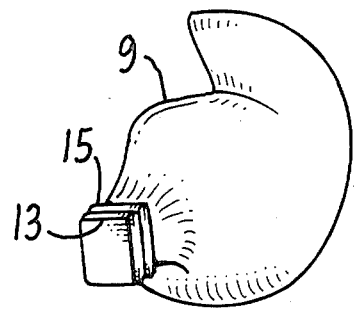
FIG. 4 is a rear perspective view of the plug.
Figure 5:
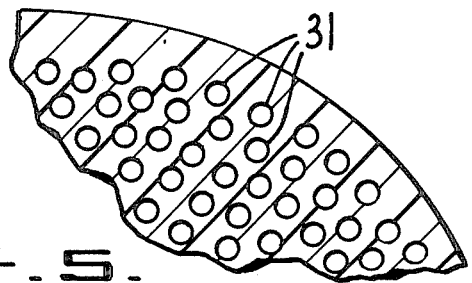
FIG. 5 is a sectional view of a portion of the plug showing the closed cell structure of the foam.

As best shown in FIG. 5, the plug of the present invention is made of a slow recovery closed cell, elastomeric foam. A multitude of closed cells 31 provides a large number of convex and concave surfaces which tend to greatly dissipate and attenuate sound waves passing through the plug. In addition, the convex shape of surface 6, as shown best in FIG. 2, tends to reflect and dissipate sound waves as they initially strike the plug.

The plug is molded by reaction injection resulting in a skin 21 covering the entire plug rendering it impervious to dirt and water. This smooth surface lends itself to washing with soap and water as well as cleansing with alcohol. This smooth surface has a much longer reusable life than die cut foam plugs having an open celled surface preventing adequate cleaning for reuse.

The plug is held in place by pressure against the tragus and antihelix and the internal knob filling the meatus.

I claim:

1. An earplug made of solid, slow recovery foam, having an inwardly extending conical portion adapted to fit into and fill the auricle, and said conical portion extending into the outer portion of the auditory canal, terminating in a rectangular knob with a flat solid wall, said knob sealing off the meatus of the external ear canal without substantially penetrating the external ear canal, and having an enlarged external flange of more than twice the cross-sectional area of the external ear canal, the external surface of said plug being convex to reflect away sound whereby the convex surface provided by the external surface of the earplug and the multitude of cells within the body of the foam earplug dramatically reflect and attenuate sound and whereby a sound and water seal is formed at the auricle.

2. The earplug of claim 1 having a skin surrounding the entire plug which is nearly impervious to dirt and water and which may be washed with soap, water and alcohol.

3. The earplug of claim 1 wherein said rectangular knob comprises a double flange.

* * * * *